US009228261B2

(12) United States Patent
Brcka

(10) Patent No.: US 9,228,261 B2
(45) Date of Patent: Jan. 5, 2016

(54) SYSTEM AND METHOD FOR TISSUE CONSTRUCTION USING AN ELECTRIC FIELD APPLICATOR

(75) Inventor: Jozef Brcka, Austin, TX (US)

(73) Assignee: Tokyo Electron Limited, Tokyo (JP)

( * ) Notice: Subject to any disclaimer, the term of this patent is extended or adjusted under 35 U.S.C. 154(b) by 441 days.

(21) Appl. No.: 13/823,701

(22) PCT Filed: Jul. 31, 2012

(86) PCT No.: PCT/US2012/049056
§ 371 (c)(1),
(2), (4) Date: Mar. 14, 2013

(87) PCT Pub. No.: WO2013/019814
PCT Pub. Date: Feb. 7, 2013

(65) Prior Publication Data
US 2013/0192990 A1 Aug. 1, 2013

Related U.S. Application Data

(60) Provisional application No. 61/514,461, filed on Aug. 2, 2011, provisional application No. 61/664,690, filed on Jun. 26, 2012.

(51) Int. Cl.
G01N 27/453 (2006.01)
G01N 27/447 (2006.01)
(Continued)

(52) U.S. Cl.
CPC . *C23C 16/50* (2013.01); *A61F 2/00* (2013.01); *B03C 5/005* (2013.01); *B03C 5/026* (2013.01);
(Continued)

(58) Field of Classification Search
CPC ...... C12N 13/00; C12M 3/00; C12M 3/0006; B03C 5/005
See application file for complete search history.

(56) References Cited

U.S. PATENT DOCUMENTS 7,323,096 B2 1/2008 Yoshida et al.
7,744,737 B1 6/2010 James et al.
(Continued)

FOREIGN PATENT DOCUMENTS

DE 10 2006 023 238 A1 11/2007
TW 200300464 6/2003
WO 2007116406 A1 10/2007

OTHER PUBLICATIONS

Albrecht et al. "Dielectrophoretic Cell Patterning Within Tissue Engineering Scaffolds," Proceedings of the Second Joint EMBS/BMES Conference Houston, TX, USA, Oct. 23-26, 2002.*
(Continued)

*Primary Examiner* — Alexander Noguerola
(74) *Attorney, Agent, or Firm* — Wood, Herron & Evans, LLP

(57) ABSTRACT

A method and apparatus are provided for constructing tissue from cells or other objects by application of temporally and spatially controlled electric fields. Electric field applicators expose a substrate (32) to the electric field controlled to affect the processing medium (28) to achieve a processing effect on the construction of tissue on the substrate (32). Electrical bias is selected to interact with dipole properties of the medium (28) to control the movement of suspended dielectrophoretic cells or other particles in the medium (28) or at the substrate (32). The motion of suspended particles may be affected to cause suspended particles of different properties to follow different paths in the processing medium (28), which may be used to cause the suspended particles to be sorted. The processing medium (28) and electrical bias may be selected to affect the structure, or orientation, of one or more layers on the substrate (32).

25 Claims, 12 Drawing Sheets

(51) Int. Cl.

| | |
|---|---|
| *C23C 16/50* | (2006.01) |
| *C12M 3/00* | (2006.01) |
| *B03C 5/00* | (2006.01) |
| *H01J 37/32* | (2006.01) |
| *C12M 1/26* | (2006.01) |
| *B03C 5/02* | (2006.01) |
| *A61F 2/00* | (2006.01) |
| *H01L 21/02* | (2006.01) |
| *H01L 21/67* | (2006.01) |
| *C23C 16/04* | (2006.01) |
| *C23C 16/48* | (2006.01) |

(52) U.S. Cl.
CPC ............... *C12M 3/00* (2013.01); *C12M 21/08* (2013.01); *C12M 33/00* (2013.01); *C23C 16/04* (2013.01); *C23C 16/48* (2013.01); *H01J 37/32009* (2013.01); *H01J 37/32697* (2013.01); *H01L 21/02612* (2013.01); *H01L 21/67011* (2013.01)

(56) References Cited

U.S. PATENT DOCUMENTS

| | | |
|---|---|---|
| 7,857,952 B2 | 12/2010 | Yoshida et al. |
| 7,867,409 B2 | 1/2011 | Brcka |
| 2004/0045837 A1 | 3/2004 | Yoshida et al. |
| 2004/0096430 A1 | 5/2004 | Bauer |
| 2005/0032204 A1 | 2/2005 | Rodgers et al. |
| 2008/0138797 A1 | 6/2008 | Hunt et al. |
| 2009/0314644 A1 | 12/2009 | Golan et al. |
| 2011/0076734 A1* | 3/2011 | Zhou et al. ............... 435/173.1 |
| 2011/0079513 A1 | 4/2011 | Stelzle et al. |
| 2011/0129892 A1* | 6/2011 | Umezu et al. ............. 435/174 |

OTHER PUBLICATIONS

Sebastian et al., "Tissue Engineering With Electric Fields: Immobilization of Mammalian Cells in Multilayer Aggregates Using Dielectrophoresis," Biotechnology and Bioengineering, vol. 98, No. 3 Oct. 15, 2007.*

Product description of the Gilson Peristaltic Pump—Minipuls® 3, publication date unknown, downloaded Jul. 24, 2015.*

Taiwan Intellectual Property Office, Examination Opinion issued in corresponding TW Patent Application No. 101128013, issued Aug. 25, 2014, with English Translation, 15 pp.

Taiwan Intellectual Property Office, Examination Opinion issued in related TW Patent Application No. 101128017, issued Dec. 27, 2014, with English Translation, 15 pp.

European Patent Office, International Search Report and Written Opinion in corresponding PCT Application No. PCT/US2012/049040, mailed Mar. 6, 2013, 12 pp.

European Patent Office, International Search Report and Written Opinion in corresponding International Application No. PCT/US2012/049056, mailed May 17, 2013, 11 pp.

Espacenet, EPO English Machine Translation of Application No. DE 10 2006 023 238 (A1), Published Nov. 22, 2007, http://worldwide.espacenet.com, retrieved Jul. 19, 2013, 12 pp.

Chen et al., "Aligning single-wall carbon nanotubes with an alternating-current electric field," Appl. Phys. Lett. 78 (23):3714-3716, 2001.

Dimaki et al., "Dielectrophoresis of carbon nanotubes using microelectrodes: a numerical study," Nanotechnology, 15:1095-1102, 2004.

Ho et al., "Rapid heterogeneous liver-cell on-chip patterning via the enhanced field-induced dielectrophoresis trap," Lab Chip, 6:724-734, 2006.

* cited by examiner

SYSTEM AND METHOD FOR TISSUE CONSTRUCTION USING AN ELECTRIC FIELD APPLICATOR

CROSS-REFERENCE TO RELATED APPLICATIONS

This application is a national phase application of International Application Ser. No. PCT/US12/49056, filed Jul. 31, 2012, which claims the benefit of and priority to prior filed Provisional Application Ser. No. 61/514,461, filed Aug. 2, 2011, and Provisional Application Ser. No. 61/664,690, filed Jun. 26, 2012, the disclosure of each is expressly incorporated herein by reference, in its entirety. This application is also related to commonly assigned International Application Ser. No. PCT/US12/49040, entitled METHOD AND DEVICE FOR CONTROLLING PATTERN AND STRUCTURE FORMATION BY AN ELECTRIC FIELD filed Jul. 31, 2012 by the inventor hereof, hereby expressly incorporated herein by reference.

FIELD OF THE INVENTION

This invention relates to the formation of patterns or structures, particularly by film formation on substrates, utilizing nanometer to micron scale objects and, more particularly, to devices and methods utilizing electric field applicators in tissue fabrication.

BACKGROUND OF THE INVENTION

Developments in nanotechnology, the manipulation of matter on the scale of 1 nm to 100 nm, have yielded materials and devices with applicability in medicine, electronics, and energy production, to name a few. Conventionally, there have been two approaches to continued developments in nanotechnology: bottom-up and top-down. Bottom-up approaches arrange nano-components into complex assemblies and have been useful in molecular assembly, atomic force microscopy, and DNA engineering. Top-down approaches create smaller devices by utilizing the influences of larger devices. For example, atomic layer deposition ("ALD") is a process by which semiconductor elements are built at atomic-layer scales.

However, these conventional nanotechnology methods and devices are not readily adaptable to enhancing or suppressing spatio-temporal electric field distributions so as to facilitate desired intercellular interactions. With improved spatial resolution of the electric fields, manipulation of nano-objects may become more reliable and efficient for bio-printing, bio-sensor fabrication, and tissue fabrication.

SUMMARY OF THE INVENTION

The present invention overcomes the foregoing problems and other shortcomings and drawbacks of the known, conventional methods of tissue fabrication. While the present invention will be described in connection with certain embodiments, it will be understood that the present invention is not limited to these embodiments. To the contrary, this invention includes all alternatives, modifications, and equivalents as may be included within the scope of the present invention.

In accordance with the present invention, the construction of tissue upon a substrate with the use of micro-or-nano size cells or other objects is enhanced by the application and control of electric fields. In certain embodiments of the present invention, the construction of tissue upon a substrate is enhanced by the application and control of temporally and spatially controlled electric fields.

According to various embodiments of the invention, a processing apparatus is provided having a processing chamber configured to receive a processing medium that is subject to being affected by an electric field while constructing the tissue upon the substrate and a substrate holder for holding a substrate to be processed within the chamber. The apparatus is provided with at least one electric field applicator that is operable to expose the substrate during construction of the tissue to the electric field, which may be a spatial-temporal electric field, that is capable of affecting the processing medium, objects suspended in the processing medium, for example cells, or the substrate, when the electric field applicator is electrically energized by an electrical bias. The electric field applicators may be addressable by a controller and may be interchangeable. A distribution coupling unit is provided that is operable to couple an electrical bias to the at least one electric field applicator to thereby energize the electric field applicator.

A controller is provided to operate the apparatus to control the characteristics of the applied electric field to affect the processing medium to achieve a processing effect on the construction of tissue on the substrate. The processing medium may be a gas or a liquid. An electric field applicator may be located outside the processing chamber and transmit the electric field to the substrate, or be located inside the processing chamber, such as adjacent the substrate. The electric field processing apparatus may be of a size substantially equal to the size of the substrate or of a size smaller than the size of the substrate and configured to be scanned across the substrate.

According to certain embodiments of the invention, a processing apparatus is provided having a processing chamber configured to receive a processing medium having dipole properties that are subject to being affected by an electric field while processing a substrate; a substrate holder for holding a substrate to be processed within the chamber. The apparatus is provided with at least one electric field applicator that is operable to expose the substrate during processing to the electric field, for example a spatial-temporal electric field, that is capable of affecting the processing medium, particles therein or the substrate, when the electric field applicator is electrically energized by an electrical bias selected to interact with the dipole properties of the medium or particles therein. The electric field applicators may be addressable by a controller and may be interchangeable. A distribution coupling unit is provided that is operable to couple a time-varying electrical bias to the at least one electric field applicator to thereby energize the electric field applicator in a way that will affect the medium or the particles. A controller is provided to operate the apparatus to control characteristics of the applied electric field to affect the processing medium to achieve a desired processing effect. The processing medium may be a gas or a liquid.

An electric field applicator may be located outside the processing chamber and transmit the electric field to the substrate, or be located inside the processing chamber, such as adjacent the substrate. The electric field processing apparatus may be of a size substantially equal to the size of the substrate or of a size smaller than the size of the substrate and configured to be scanned across the substrate. Where the size of the substrate, it may be a stationary part of the apparatus and activated and addressed by grid structure or other logic circuitry according to an appropriate spatial and time-domain algorithm. Where smaller, it may be controlled by some such algorithm as well as motion with respect to the substrate.

According to certain embodiments of the invention, the electric field processing may include an irradiation source, such as, for example, a microwave radiation source, an ultraviolet radiation source, or an infrared radiation source. Further, the electrical bias may include a DC potential component, an AC or RF potential, a switched DC potential, another time varying waveform, or a combination thereof. The potential may be applied to the electric field by a distribution coupling unit through direct electrical contact, or by capacitive or inductive coupling. The apparatus may include a magnetic field generator, an acoustic field generator, or an optical force generation device to further influence the nano-objects.

In certain embodiments of the processing apparatus, the processing medium and electrical bias may be configured for selective localized deposition of layers on the substrate. The time-varying electrical bias in many embodiments varies at less than 10,000 Hz, and typically at less than 1,000 Hz.

According to certain methods of the present invention, electric field processing of a substrate is carried out with a processing apparatus by supporting a substrate to be processed in a chamber, introducing a processing medium into the chamber which may also have cells or other particles carried by the medium, with the medium and particles possessing a dipole configuration when subjected to an appropriate electrical field. Then, an electrical bias, for example, a spatially and time-varying electrical bias, may be applied to at least one electric field applicator to create the electric field appropriate to affect the processing medium or particles therein to construct the tissue in a desired way in the vicinity of or at the surface of the substrate. The processing may include constructing one or more layers of cells on the substrate to build multilayered tissue, for example, or controlling the movement of suspended dielectrophoretic cells particles in the medium or onto the substrate. In some embodiments, the motion of suspended particles may be affected to cause suspended particles of different properties to follow different paths in the processing medium, which may be used to cause the suspended particles to be sorted. Further, the suspended particles may be bioagents, and the motion of suspended particles may be controlled in part by applying a static or time-varying electrical bias so as to deposit the suspended particles at predetermined locations on the substrate.

In some embodiments, irradiating of the substrate may be carried out, for example, with microwave radiation, ultraviolet radiation, or infrared radiation sources. Depositing or modifying a layer on the substrate may also be carried out. In some embodiments, the processing medium and electrical bias may be selected to affect the structure, or orientation, or both, of a first deposited layer on the substrate, and may do so differently for different layers on the substrate.

In the illustrated embodiment of the invention, an electric field processing system for building a tissue from cells is provided that comprises a processing chamber configured to receive a substrate at one end thereof upon which the tissue is to be built. An electric field applicator disposed proximate the substrate in the chamber, for example, but not necessarily, at an end of the chamber opposite the substrate. The at least one electric field applicator is configured to apply an electric field to the substrate and a processing region of the processing chamber proximate the substrate. The applicator may include a grid electrode. The apparatus also includes a distributing bias unit configured to supply an electrical bias to the at least one electric field applicator, a fluid delivery system for delivering cells and fluids used in building the tissue, and at least one power supply for providing electric power to the distributing bias unit. The applicator may be provided with a manipulator for positioning the electric field applicator with respect to the substrate. A control system is further provided for controlling the electric field applicator, manipulator, and the at least one power supply.

In the illustrated embodiments, the at least one electric field applicator is configured to impart a predetermined behavior to either the cells or fluids or both, and in some embodiments may be interchangeable with another electric field applicator configured to impart a different behavior on either the cells or fluids or both. The processing system may include one or more of a cell reservoir for providing the cells for building of the tissue and in fluid communication with the fluid delivery system, a hydrogel reservoir for providing a hydrogel to the fluid delivery system, a stabilization liquid reservoir for providing a stabilizing liquid to the fluid delivery system, and a flush liquid reservoir for providing a flush liquid to the fluid delivery system. The system may also include at least one source of electromagnetic radiation configured for irradiating the substrate or tissue or both, which may include one or more infrared radiation sources, one or more ultraviolet radiation sources, one or more visible light radiation sources, and/or one or more microwave radiation sources. The system may also include a temperature control system for spatially and temporally varying the temperature of the substrate, or the tissue, or both; the temperature control system may be controlled by the control system of the apparatus.

In the illustrated embodiment, the fluid delivery system may include at least one microfluidic device. Also, the manipulator may be configured to vary the distance between the electric field applicator and the substrate, or to vary the azimuthal orientation of the electric field applicator with respect to the substrate, or both. Further, the at least one electric field applicator may include a plurality of microelectrodes, which may be electrically insulated from the processing region. In addition, the electric field is spatially-varying, time-varying, or both.

The illustrated embodiment of the system is operable in building tissue from cells by supplying a processing medium through a fluid delivery system to a processing region, supplying cells through the fluid delivery system to the processing region, and applying an electrical bias to at least one electric field applicator to generate an electric field, with the electric field being configured to controllably select, transport, orient, arrange, or manipulate cells in the processing region to build the tissue on the substrate. The method may further include applying a second electrical bias to at least one electric field applicator to generate a second electric field that is different than the first electric field and is configured to differently controllably select, transport, orient, arrange, or manipulate cells in the processing region to build the tissue on the substrate. In addition, the method may include positioning one or more of the electric field applicators, using a manipulator, at a pre-set distance from the substrate, or at a pre-set azimuthal orientation with respect to the substrate, or both.

The method may also include irradiating the tissue with at least one of infrared radiation, visible light radiation, ultraviolet radiation, and microwave radiation.

These and other embodiments of the invention may be readily apparent from the following detailed description in which:

BRIEF DESCRIPTION OF THE DRAWINGS

The accompanying drawings, which are incorporated in and constitute a part of this specification, illustrate embodiments of the present invention and, together with a general description of the invention given above, and the detailed description given below, serve to explain the invention.

DETAILED DESCRIPTION

Figure 1:
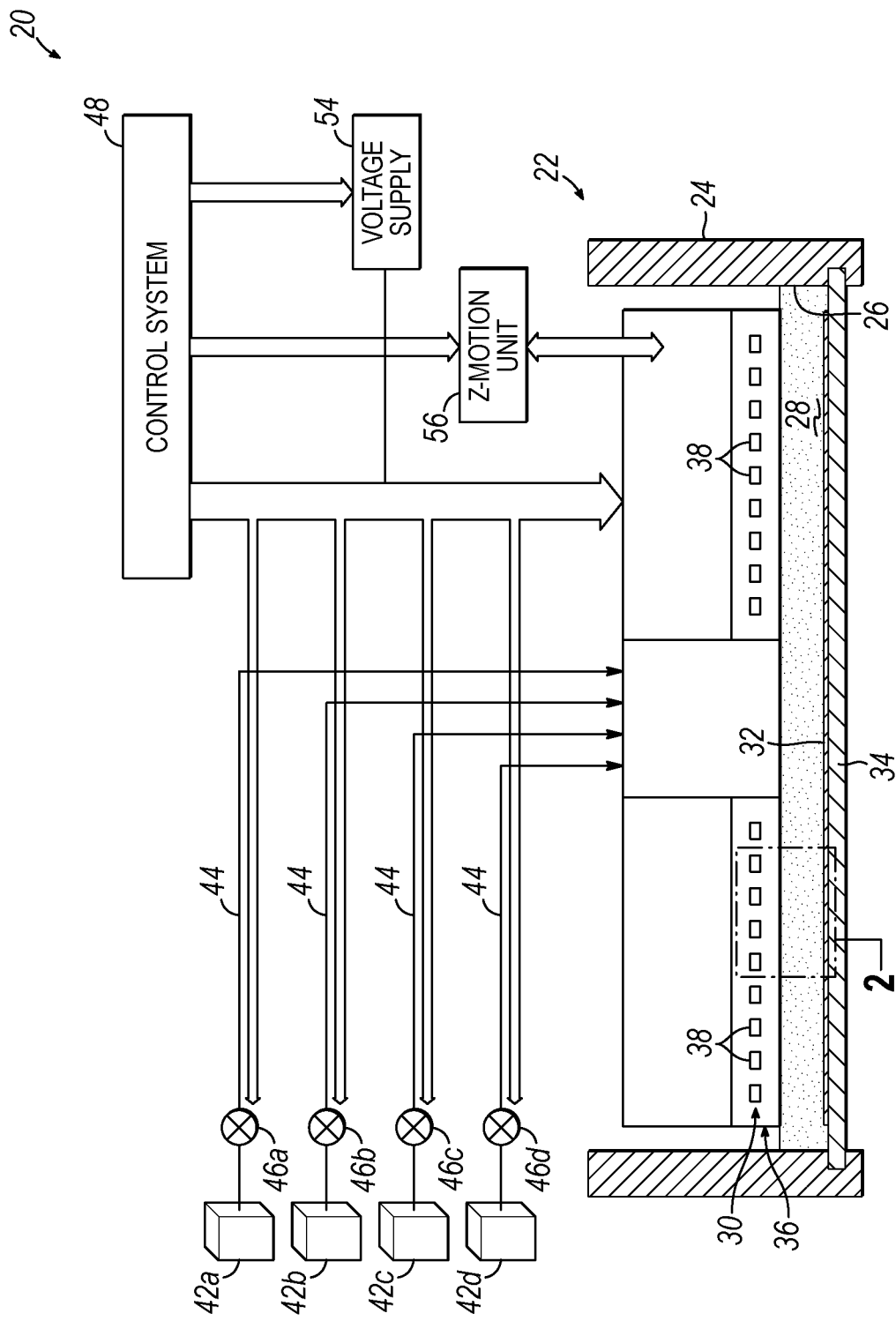
FIG. 1 is a schematic illustration of a tissue fabrication system in accordance with one embodiment of the present invention.
Figure 2:
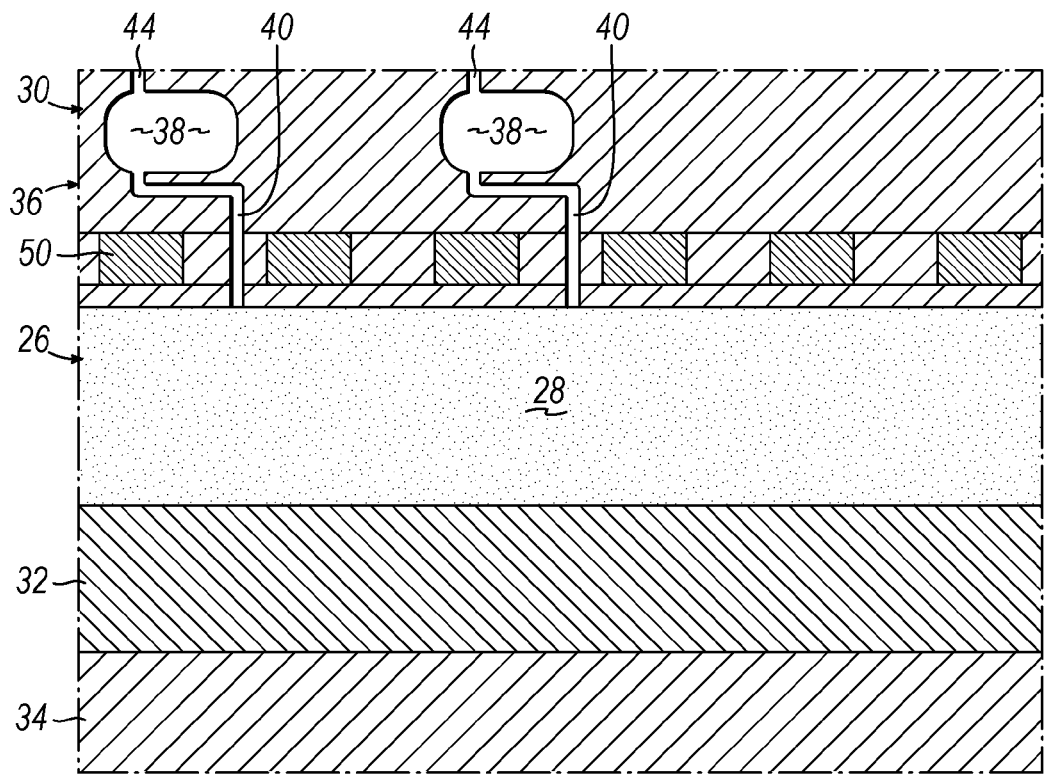
FIG. 2 is an enlarged view of the portion of the processing chamber encircled in FIG. 1.

With reference now to the figures, and in particular to FIGS. 1 and 2, a dynamic tissue fabrication system 20 is shown in accordance with one embodiment of the present invention. The tissue fabrication system 20 includes a processing chamber 22 having a chamber wall 24 enclosing a processing space 26, which may be filled with a processing medium 28 provided by a microfluidic system 30 described in detail below. The size of the processing space 26 is likewise dependent on the particular application and will vary accordingly; however, a processing space 26 volume ranging from about 0.1 L to several liters may be typical.

A substrate 32 residing on a substrate holder 34 is exposed to the processing space 26 and processing medium 28 contained therein and is configured to support the fabrication and growth of a tissue thereon. While not required, the substrate 32 may be a 300 mm diameter wafer having a thickness of about 800 μm.

The microfluidic system 30 may include one or more reservoirs 38 integrated within an electric field applicator ("EFA") head 36, fluidically coupled to the processing space 26 via microfluidic channels 40, and to one or more fluid supplies 42a, 42b, 42c, 42d via a plurality of microfluidic supply lines 44. The microfluidic channels 40 and microfluidic supply lines 44 may be fabricated and operated using MEMS-based technologies.

The fluids provided via fluid supplies 42a, 42b, 42c, 42d may vary on the particular cell population grown within the processing chamber 22 and may include suspended cells in 42a, hydrogel(s) in 42b for (polymers providing a scaffolding for tissue fabrication), stabilization fluids in 42c, flush liquids in 42d, and so forth. One or more valves 46a, 46b, 46c, 46d may be operatively coupled to a control system 48 and selectively controlled to provide appropriate fluids during tissue fabrication.

With specific reference now to FIG. 2, the EFA head 36, which is configured to generate an electric field within the processing space 26 and in proximity to the substrate 32, includes one or more electrodes 50 and associated bias connections 52, which may be a permanent fixture coupled to the processing chamber 22 or releaseably coupled thereto for interchangeability for particular use and applications. By way of the bias connections 52, the electrodes 50 are operatively coupled to a voltage supply 54 (FIG. 1) that is configured to generate a time dependent current (AC or switching DC) having a selected waveform.

Figure 8A:
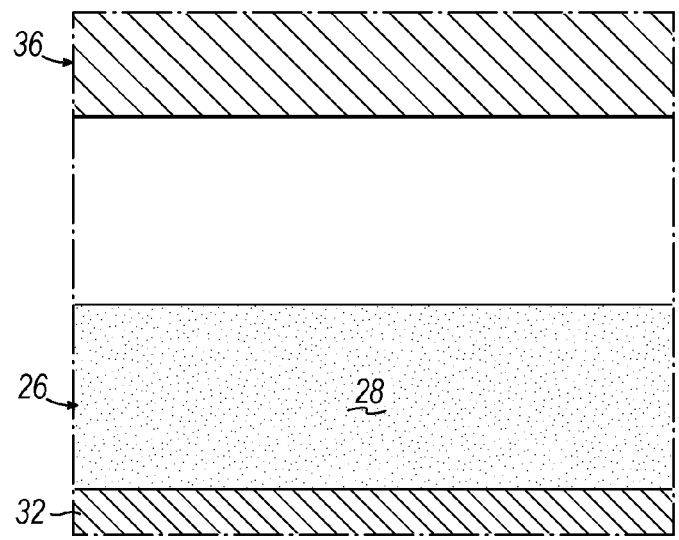
FIG. 8A-8P are diagrammatic views of tissue fabrication within the processing chamber of the system of FIG. 1 and according to one embodiment of the present invention.
Figure 8B:
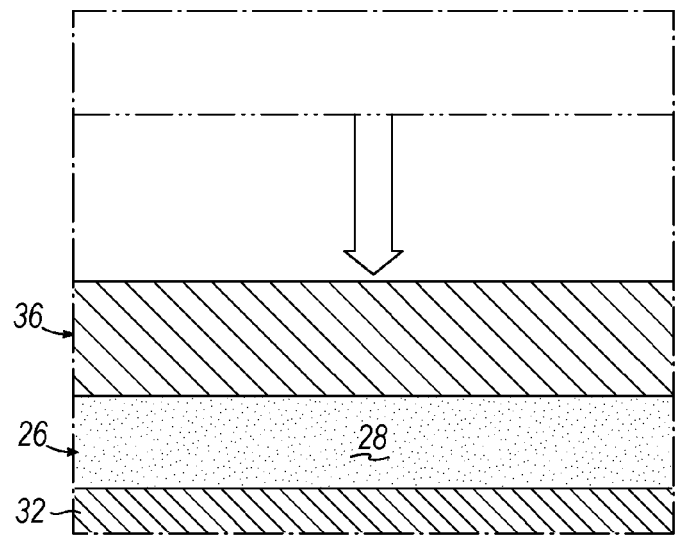
Figure 8C:
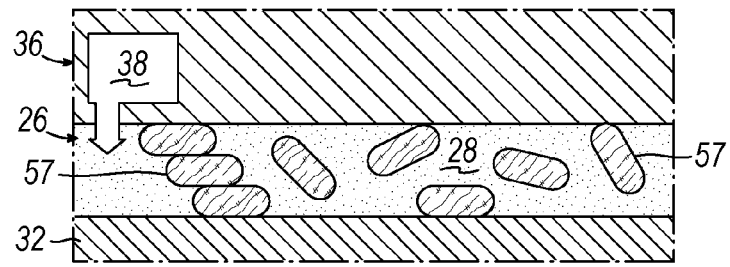
Figure 8D:
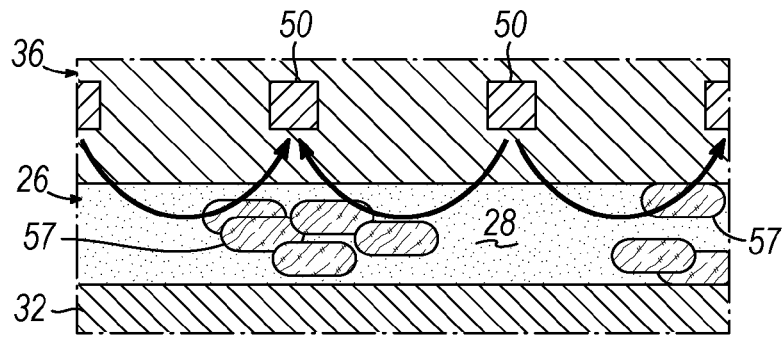
Figure 8E:
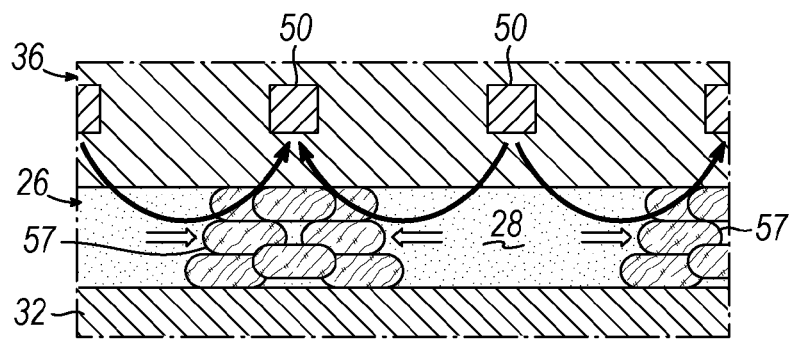

The shape, size, and configurations of the electrodes 50 may vary on the particular application and cell line used in the tissue fabrication, but are described generally in International Application No. PCT/US2012/049040, filed on even date herewith and entitled METHOD AND DEVICE FOR CONTROLLING PATTERN AND STRUCTURE FORMATION BY AN ELECTRIC FIELD. Briefly, the electrodes 50 may be arranged in a grid-like pattern that is congruent to the size of the substrate 32, one or more of which be selectively operable to define a plurality of zones 55 (FIG. 5), each zone 55 (FIG. 5) being an area in which a discrete force may be applied to a cell 57 (FIG. 8C). If desired, two or more adjacent zones 55 (FIG. 5) having the same (homogeneous) or different (heterogeneous) electric fields may define a subgroup that is operable to generate a selected force onto the cells 57 (FIG. 8C).

The electrodes 50 (or a subgroup thereof) are configured to control the manipulation, movement, orientation, and alignment of cells comprising the fabricated tissue. If necessary, additional energy sources may also be used for further control, including, for example, a radiation source. The wavelength of the radiation source may be selected on the particular desired chemistry, such as activation or deactivation, the opacity of the processing medium, the material comprising the substrate, and so forth. Generally, wavelength may be within the UV, IR, or microwave portions of the electromagnetic spectrum. Radiation may be applied from above or below the wafer. For instance, quartz is transparent to radiation having a wavelength ranging from about 200 nm to about 2 μm while silicon is almost transparent for wavelengths within the IR range (from about 2 μm to about 10 μm), although absorbance will depend on temperature. Equivalent energy level for IR radiation ranging from about 1 μm to 10 μm is about 1.24 eV to about 0.12 eV.

Electrodes 50 may be produced by thin film or MEMS technology and, for example, may be integrated within a substrate of silicon, ceramic, TEFLON, or glass. The EFA head 36 may be permanent (built-in) or interchangeable to utilize various electrode configurations within the same tissue fabrication system 20, which may be interchangeable via an automated robotic system (not shown), or manually.

With reference again to FIG. 1, the EFA head 36 may be further operatively coupled to a z-axis motor 56, which is configured to move the EFA head 36 relative to the substrate 32 and vary the processing space 26 therebetween. Known instrumentation may be used for adjusting the distance, which may be accomplished in a continuous or stepwise fashion.

Figure 3:
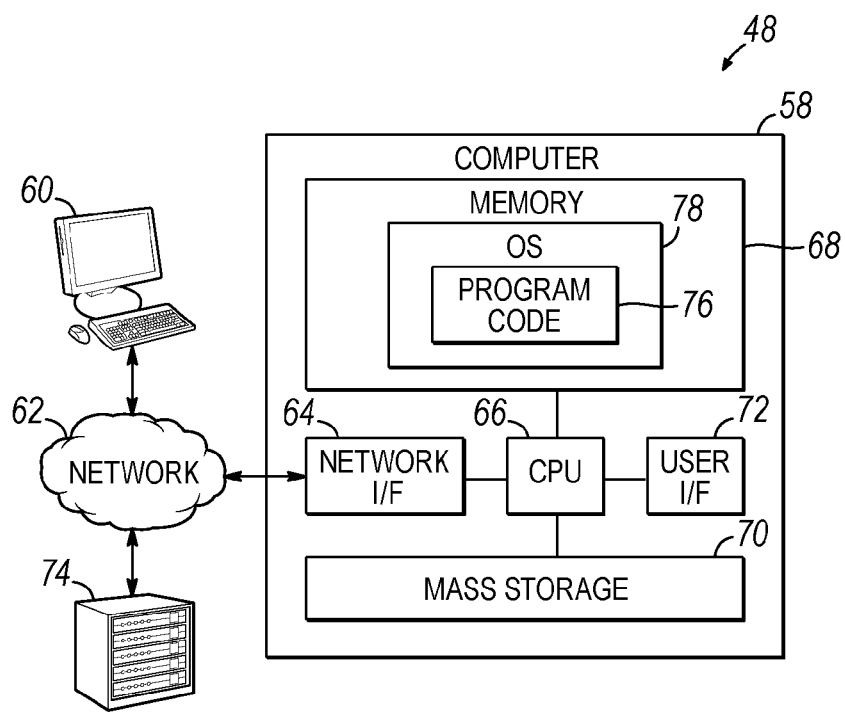
FIG. 3 is a diagrammatic view of a computer for use in controlling operation of the processing chamber of FIG. 1 and in accordance with embodiments of the present invention.

One or more of the voltage supply 54, z-axis motor 56, valves 46a, 46b, 46c, 46d, and bias connections 52 may be operably controlled by the control system 48, which may comprise a computer 58 as shown in FIG. 3. As shown in FIG. 3, the computer 58 may be a computer, computer system, computing system, server, disk array, or programmable device such as multi-user computers, single-user computers, handheld devices, networked devices, or embedded devices, etc. suitable for use in accordance with embodiments of the present invention. The computer 58 may be implemented with one or more networked computers 60 using one or more networks 62, e.g., in a cluster or other distributed computing system through a network interface (illustrated as "NETWORK I/F" 64). The computer 58 will be referred to as "computer" for brevity's sake, although it should be appreciated that the term "computing system" may also include other suitable programmable electronic devices consistent with embodiments of the present invention.

The computer 58 typically includes at least one processing unit (illustrated as "CPU" 66) coupled to a memory 68 along with several different types of peripheral devices, e.g., a mass storage device 70 with one or more databases, an input/output interface (illustrated as "I/O I/F" 72), and the Network I/F 64. The memory 68 may include dynamic random access memory ("DRAM"), static random access memory ("SRAM"), non-volatile random access memory ("NVRAM"), persistent memory, flash memory, at least one hard disk drive, and/or another digital storage medium. The mass storage device 70 is typically at least one hard disk drive and may be located externally to the computer 58, such as in a separate enclosure or in one or more networked computers 60, one or more networked storage devices (including, for example, a tape or optical drive), and/or one or more other networked devices (including, for example, a server 74, as shown.

The CPU 66 may be, in various embodiments, a single-thread, multi-threaded, multi-core, and/or multi-element processing unit (not shown) as is well known in the art. In alternative embodiments, the computer 58 may include a plurality of processing units that may include single-thread processing units, multi-threaded processing units, multi-core processing units, multi-element processing units, and/or combinations thereof as is well known in the art. Similarly, the memory 68 may include one or more levels of data, instruction, and/or combination caches, with caches serving the individual processing unit or multiple processing units (not shown) as is well known in the art.

The memory 68 of the computer 58 may include one or more applications (illustrated as "PROGRAM CODE" 76), or other software program, which are configured to execute in combination with the Operating System 78 and automatically perform tasks necessary for controlling the electrodes 50, the bias connections 52, the voltage supply 54, and so forth, with or without accessing further information or data from the database(s) of the mass storage device 70.

Those skilled in the art will recognize that the environment illustrated in FIG. 3 is not intended to limit the present invention. Indeed, those skilled in the art will recognize that other alternative hardware and/or software environments may be used without departing from the scope of the invention.

Figure 4:
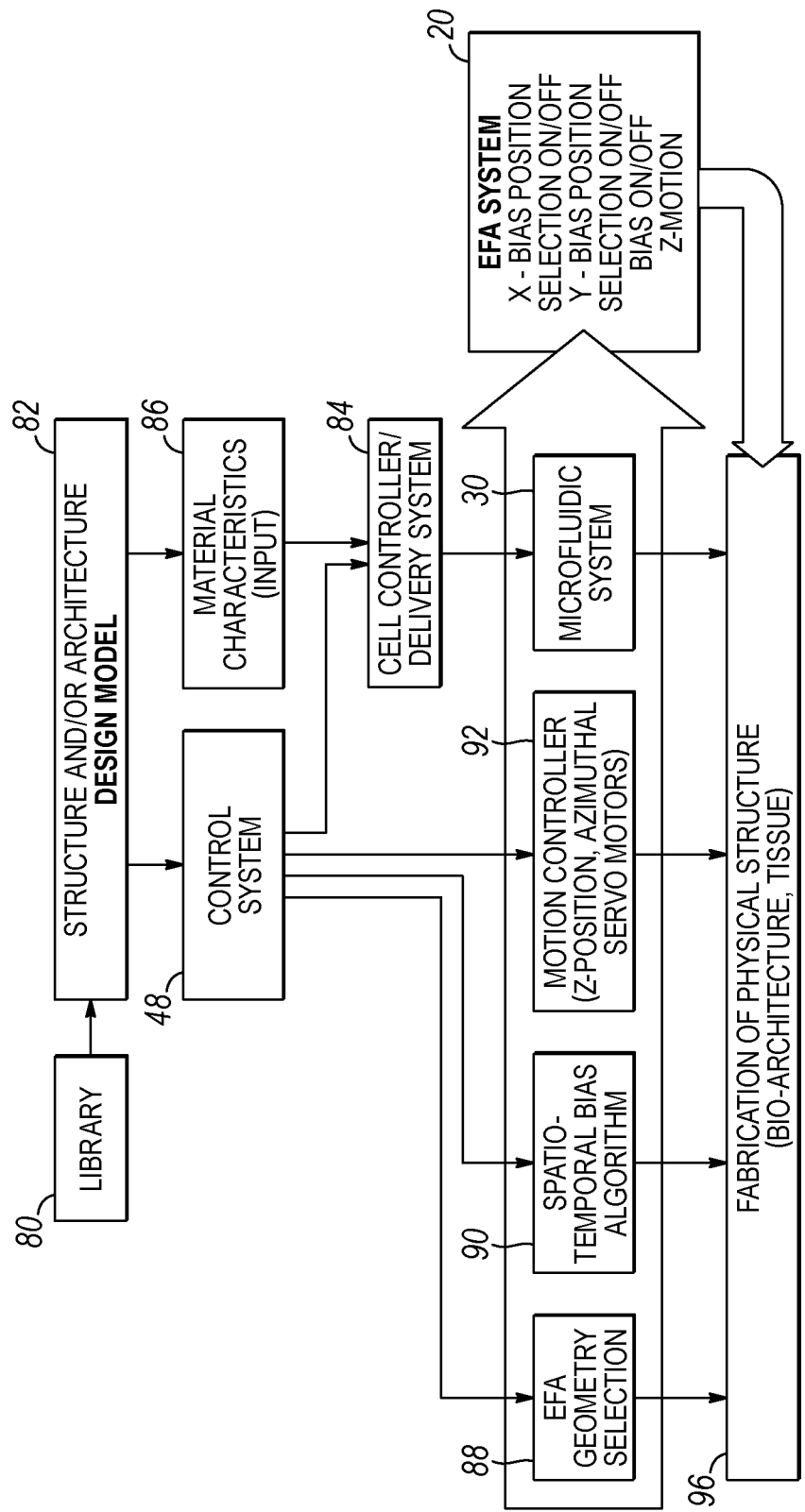
FIG. 4 is a diagrammatic view of a plurality of modules for operating the tissue fabrication system of FIG. 1 and in accordance with one embodiment of the present invention.

FIG. 4 is a diagrammatic illustration of a flow of information related to instructions, sequences, protocols, procedures, and the like (collectively referenced as "instructions") for fabricating a selected tissue. In that regard, the mass storage device 70, as noted above, may include a database, for example, an internal library 80 comprising one or more structural and/or architecture design models 82 having instructions that are directed to the control system 48 and a microfluidics system controller 84 (which may alternatively be incorporated into the control system 48). Inputs 86 from the user may also be received and directed to the microfluidics system controller 84. If desired, new models may be saved or directed to the library 80, such as by creating new descriptions. The materials and fluid delivery instructions are directed into the microfluidic system 30 for selectively controlling the release of fluids from the fluid supplies 42a, 42b, 42c, 42d via the valves 46a, 46b, 46c, 46d.

Based on the selected model 82, the fluid supplies 42a, 42b, 42c, 42d and valves 46a, 46b, 46c, 46d are activated per a processing command, which is driven by the program code 76. The processing commands bias electrodes 50 according to a particular geometry determined by an algorithm. Furthermore, the processing commands indicate a position of the EFA head 36 relative to the substrate 32 and activate and deactivate valves 46a, 46b, 46c, 46d for the transport of cell population and processing fluids into processing space 26.

Other instructions related to the arrangement of the electrodes 50 (EFA geometry selection 88), the waveforms and control of bias potential, including the duration and repetition frequency (spatio-temporal bias algorithm 90), and the z-axis motor 56 and/or other motors (motion controller 92) may be directed to the tissue fabrication system 20 for fabricating the physical tissue according thereto (fabrication of physical structure 93).

Figure 5:
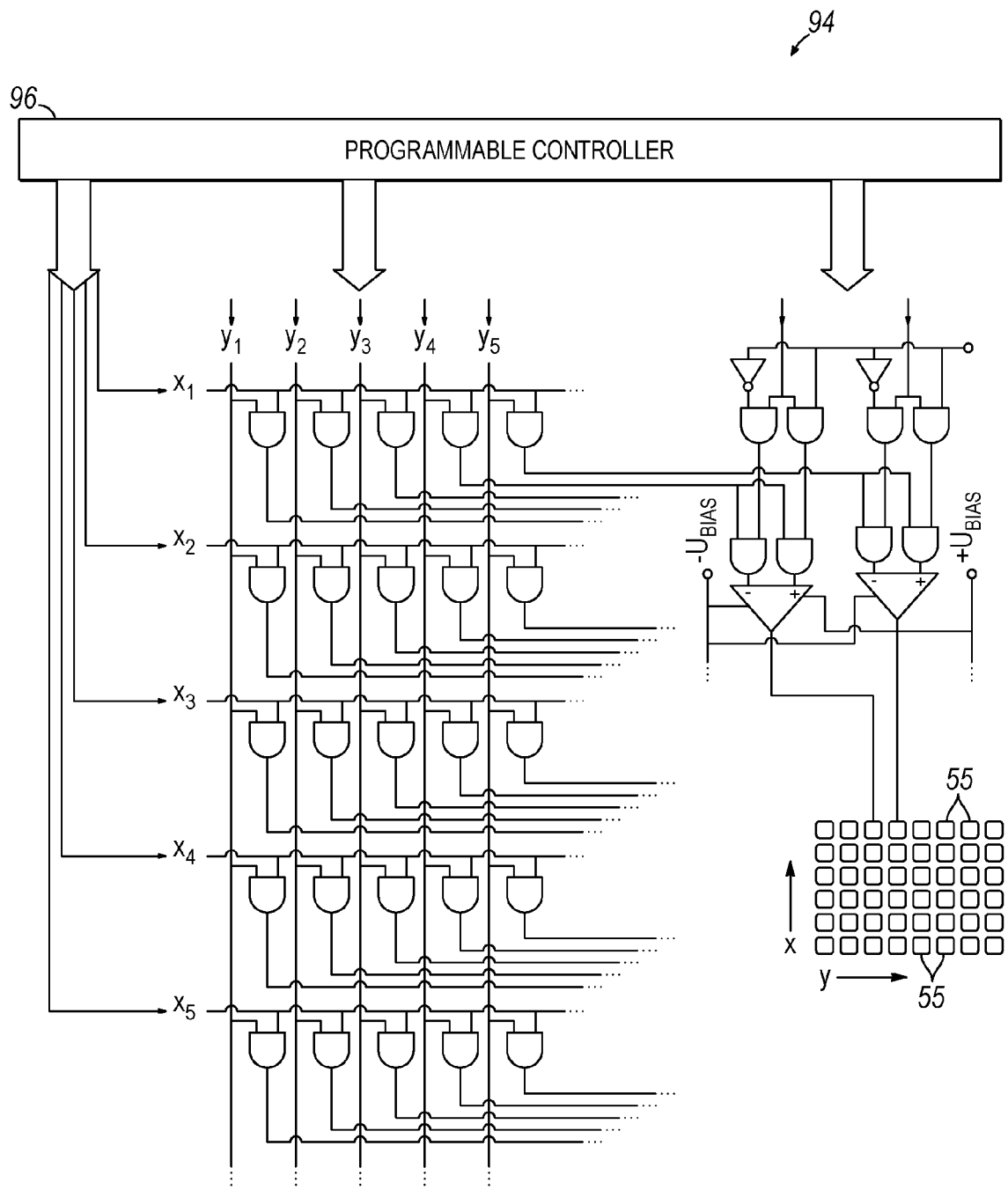
FIG. 5 is a logic diagram of a two-dimensional control system for operating an electric field applicator according to one embodiment of the present invention.
Figure 6A:
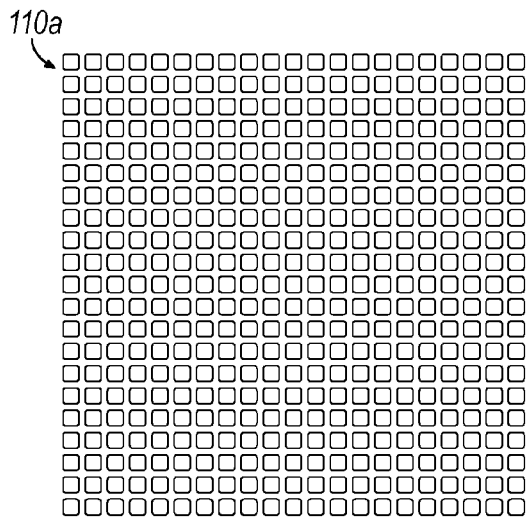
FIGS. 6A-6F are exemplary patterns provided by the two-dimensional control system of FIG. 5.
Figure 6B:
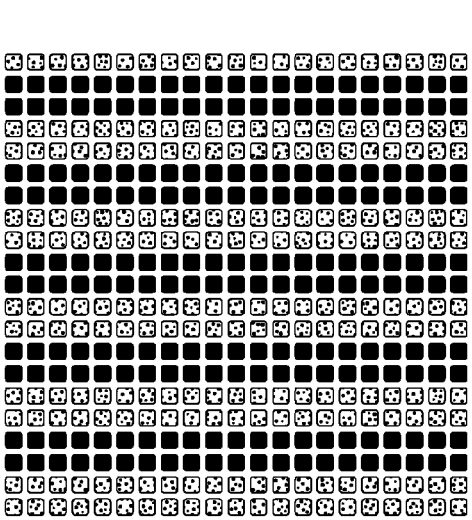
Figure 6C:
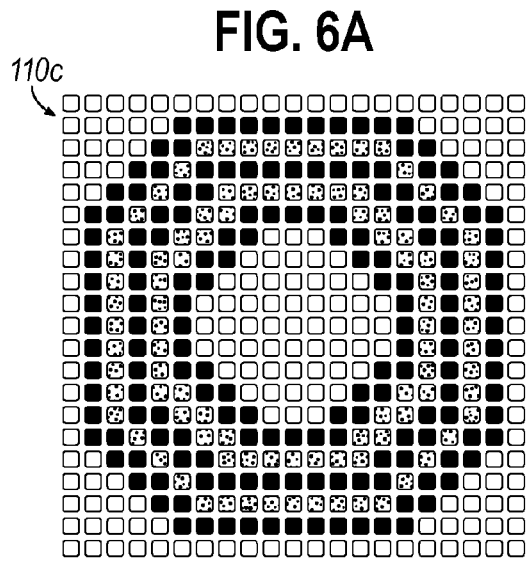
Figure 6D:
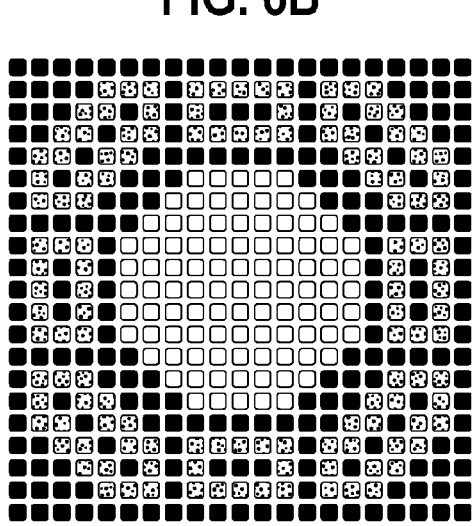
Figure 6E:
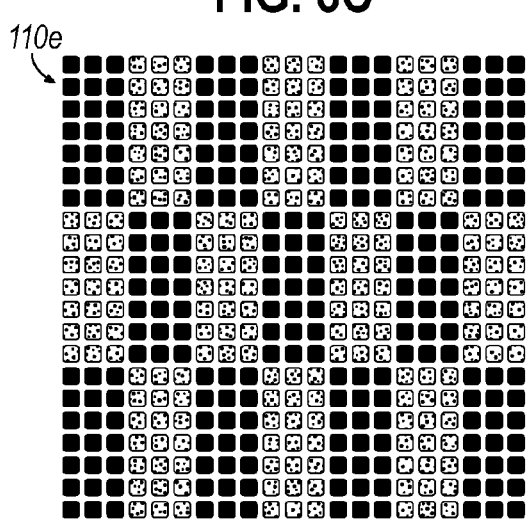
Figure 6F:
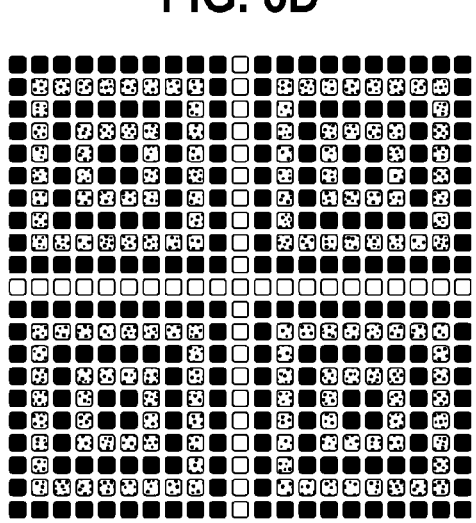

FIG. 5 illustrates the details of a simplified electronic circuit 94 according to one embodiment of the present invention for providing the logic of biasing the individual electrodes. The circuit 94 includes a programmable controller 96 for applying the algorithm into the array of electrodes. The position of a selected electrode to be biased each have particular x- and y-axis coordinates $(x_i, y_j)$, and the polarity and amplitude of an applied voltage. The circuits needed to apply potential to a grid is known technology. Several of the known schemes used to energize pixels on a display may be used to apply potentials to the areas. For example, the electrodes of the EFA may be selectively operable to define a plurality of zones. The circuitry may include a programmable controller, which may be in the form of a computer 48. Each zone may be an individual electrode or an area influenced by several electrodes in which a discrete force may be applied to a particle and/or the medium. If desired, two or more adjacent zones having the same (homogeneous) or different (heterogeneous) electric fields may define a subgroup that is operable to generate a selected force onto the particles. By specifying the function to be achieved, an electrical design engineer would be able to provide the appropriate logic. Therefore such control schemes are not described here in detail.

As a result, a time dependent, macro-pattern 110a, 110b, 110c, 110d, 110e, 110f, may be generated. FIGS. 6A-6F illustrate macro-patterns in accordance with various embodiments of the present invention and in which open pixels indicate no voltage potential, darkened pixels indicate a positive voltage potential, and shaded pixels indicate a negate voltage potential. The macro-pattern 110a, 110b, 110c, 110d, 110e, 110f is operable to generate time-varying electric fields to manipulate cells according a selected model by imposing a dielectrophoretic force. The cells accordingly move and align into an optimal position, bringing groups of cells into closer proximity, and resulting in faster agglomeration and adhesion to facilitate rapid growing of the tissue.

Figure 7:
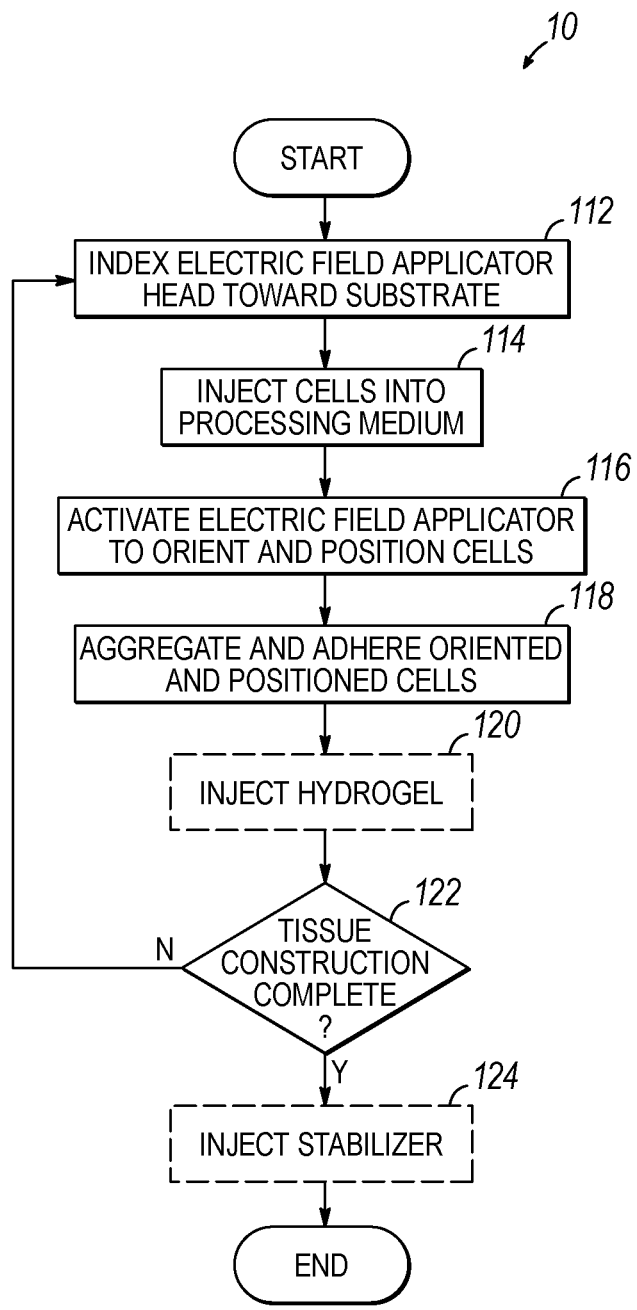
FIG. 7 is a flow chart illustrating a method of tissue fabrication using the system of FIG. 1 and in accordance with one embodiment of the present invention.
Figure 8F:
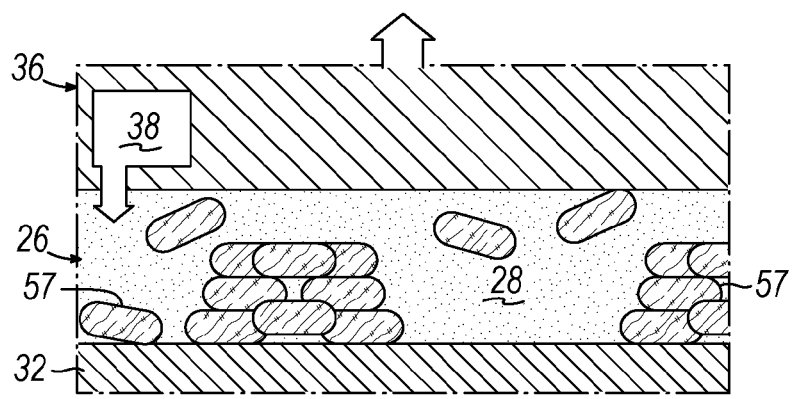
Figure 8G:
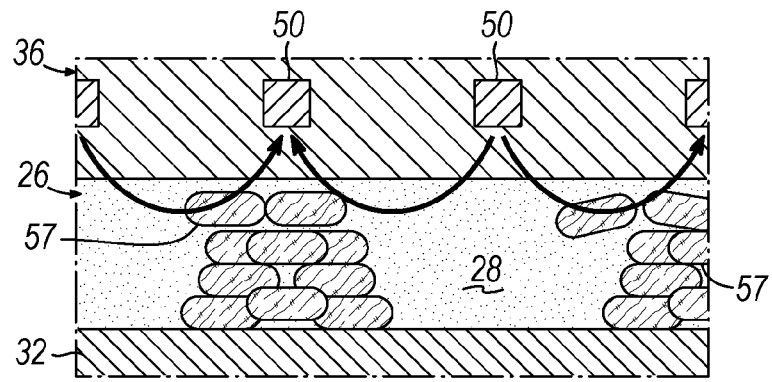
Figure 8H:
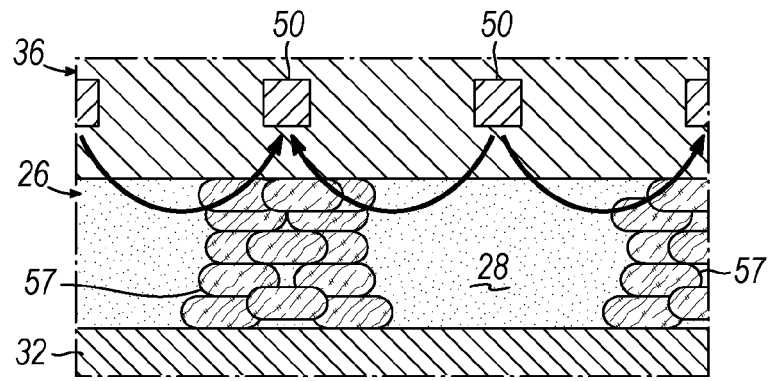
Figure 8I:
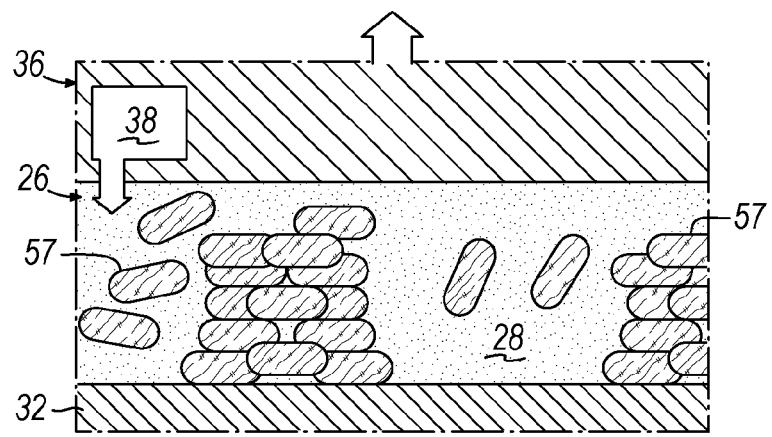
Figure 8J:
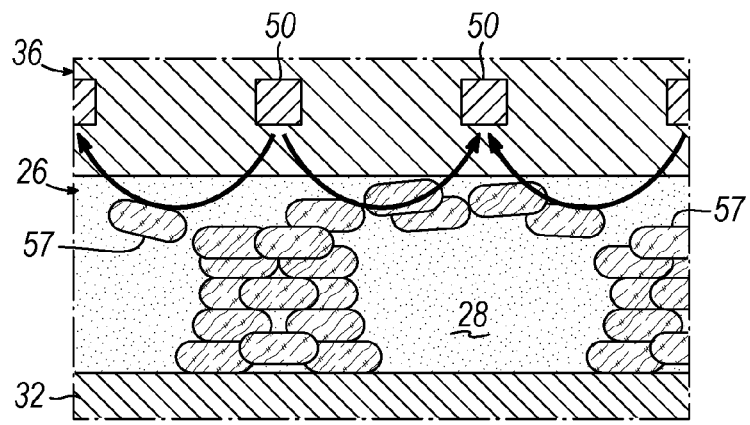
Figure 8K:
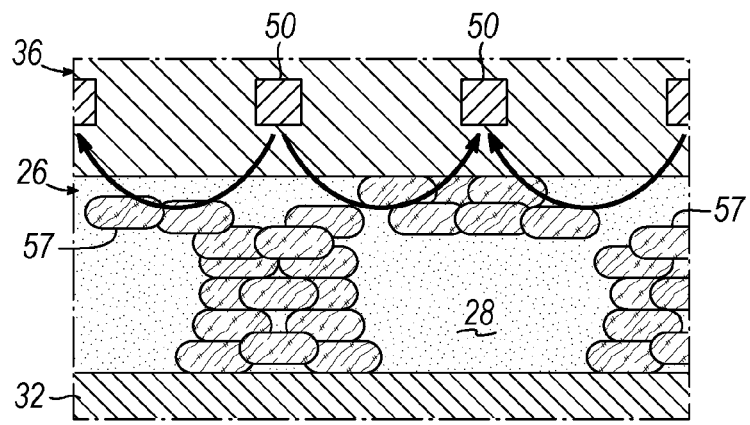
Figure 8L:
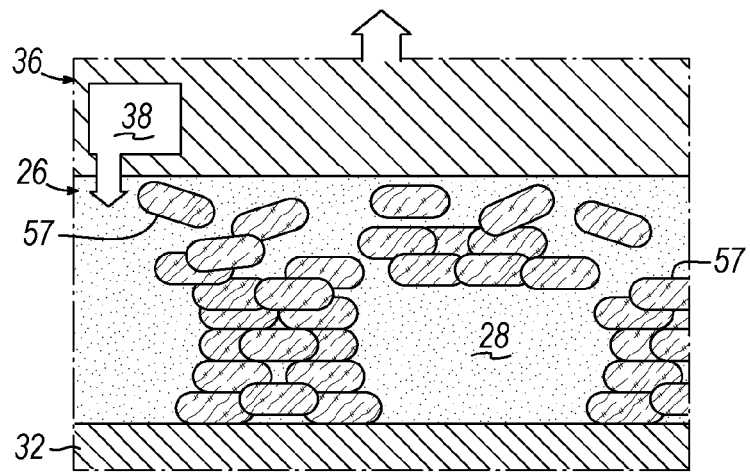
Figure 8M:
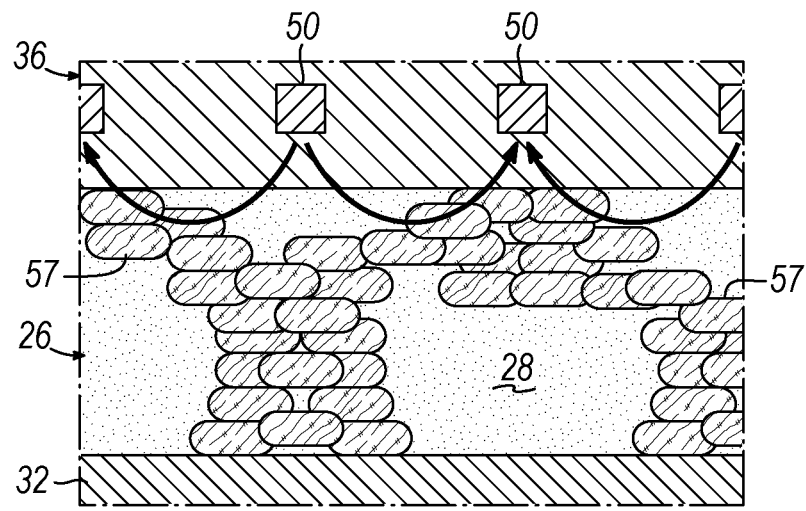
Figure 8N:
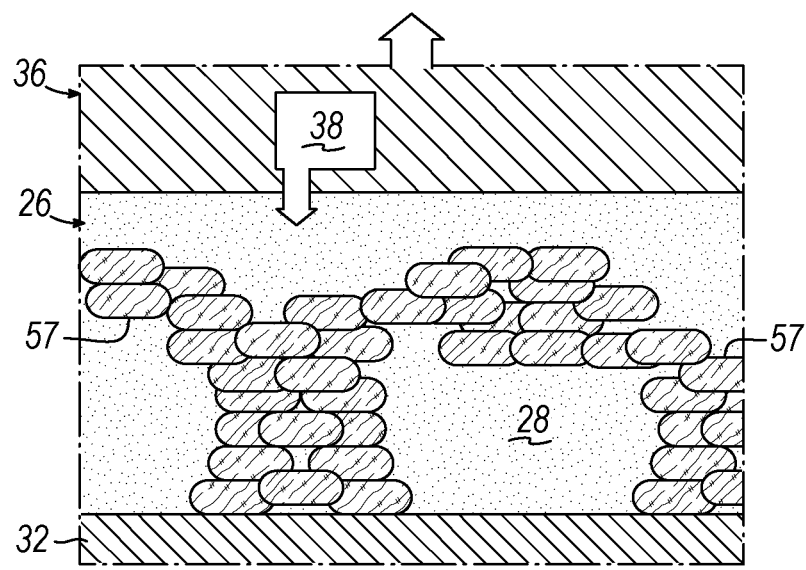
Figure 8O:
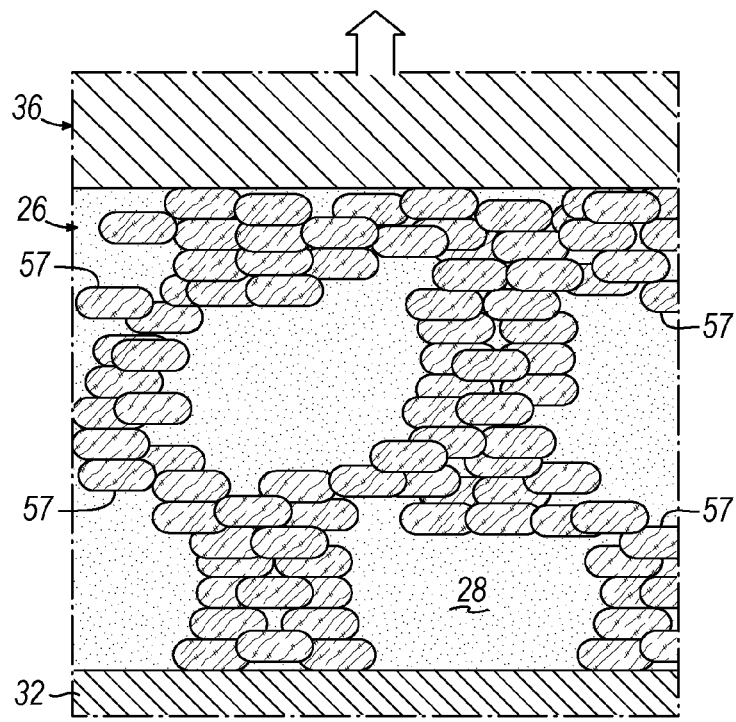
Figure 8P:
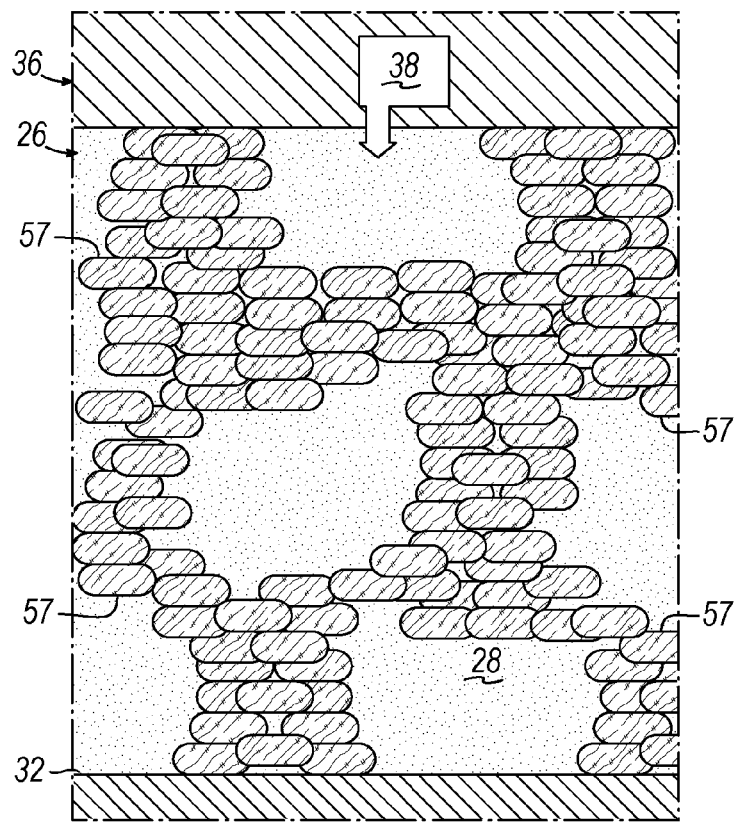

With the details of the tissue fabrication system 20 described in some detail, and turning now to FIGS. 7-8P, a method of fabricating a tissue in accordance with one embodiment of the present invention is described. FIG. 7 is a flow chart 108 illustrating one method of fabricating a tissue in accordance with one embodiment of the present invention, the fabrication being shown schematically in FIGS. 8A-8P. In that regard, and in Step 112, the EFA head 36 may be indexed toward the substrate 32 using the z-axis motor 56 and as shown in FIGS. 8A and 8B, the downward motion represented by an arrow 113. With the EFA head 36 positioned at a first distance with respect to the substrate 32, cells 72 may be injected, in Block 114, from a cell fluid supply 42a, through the valve 46a, into the microfluidic channels 40, and into the processing space 26 as shown in FIG. 8C. As there is no external force applied to the cells 57, the cells 57 diffuse throughout the processing space 26 under ambient conditions.

In Step 116, the electrodes 50 of the EFA head 36 may be biased in accordance with the spatio-temporal bias algorithm 90 so as to generate a macro-pattern 110a. The electric field resulting from the biased electrodes 50 induces a dipole within each cell such that a net force is applied to the cell, moving the cell within the processing medium accordingly. With continued biasing and in Step 118, the cells further aggregate, an adhesion forming between adjacent cells to provide an initial scaffolding for the fabricated tissue, shown in FIG. 8E. If desired, hydrogel may optionally be injected into the processing space, in optional step 120, from the appropriate supply 42b and valve 46b to further provide support to the cell arrangement.

In Step 122, a determination of whether the tissue construction is complete is made. If further construction is necessary ("No" branch of decision step 122), then the process returns to step 112 such that the EFA head 36 may be appropriately indexed with respect to the substrate 32 and the aggregated cells. As shown in FIG. 8F, tissue fabrication is incomplete, the EFA head 36 is indexed away from the aggregated cells, and additional cells are injected into the processing medium 28. FIGS. 8G and 8H illustrate the activation of the electrodes 50 (having the same macro-pattern 110a as FIG. 8D) and aggregation of the cells 57 as provided in Steps 116 and 118. Again, in FIG. 8I, the decision is made that tissue construction is incomplete ("No" branch of decision step 122) such that EFA head 36 is indexed and cells 72 are again added to the processing medium 28.

As shown in FIGS. 8J and 8K, the electrodes 50 are again activated but in accordance with another macro-pattern such that cells aggregate and adhere at a location that is different from the location of the previous aggregated cells. It would be appreciated that the order of macro-patterns here are not restricted to example provided herein.

FIGS. 8L-8N illustrate further repetition of indexing the EFA head 36, activating the electrodes 50 according to a selected macro-pattern, and inducing that aggregation and adhesion of cells.

When the tissue construction is complete ("Yes" branch of decision step 122) and as shown in FIG. 8P, the process may optionally include the injection of a stabilizer from the appropriate fluid supply 42a, which further facilitates adhesion of the aggregation of cells in the three-dimensional tissue structure.

As provided in detail herein, a tissue fabrication system is configured to provide fast manipulation of nano-objects (proteins, viruses, cells, etc.) that are sensitive to electric fields while fabricating tissues with a high throughput. The system is versatile, includes limited moving parts, limits contact between the nano-objects and the electrodes, is scalable, and is compatible with standard CMOS fabrication methods, circuits, and various types of nano-objects.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be made from such details without departing from the scope of the general inventive concept.

What is claimed is:

1. An electric field processing system for building a tissue from cells, comprising:
    a processing chamber, the processing chamber having a first end with a substrate holder positioned therein to receive a substrate upon which the tissue is to be built;
    an electric field applicator disposed proximate the substrate holder and configured to apply an electric field to a substrate positioned thereon in a processing region of the processing chamber proximate thereto;
    a distributing bias unit configured to supply an electrical bias to the at least one electric field applicator;
    a fluid delivery system for delivering cells and fluids used in building the tissue;
    a manipulator for positioning the electric field applicator with respect to a substrate positioned on the substrate holder;
    at least one power supply for providing electric power to the distributing bias unit; and
    a control system for controlling the electric field applicator, manipulator, and the at least one power supply.

2. The processing system of claim 1 wherein:
    the electric field applicator is located at a second end of the processing chamber opposite the substrate holder.

3. The processing system of claim 1, wherein the at least one electric field applicator is configured to impart a predetermined behavior to the cells or fluids or both, and is interchangeable with another electric field applicator configured to impart a different behavior on the cells or fluids or both.

4. The processing system of claim 1, further comprising:
    a cell reservoir, for providing the cells for building of the tissue, the cell reservoir being in fluid communication with the fluid delivery system.

5. The processing system of claim 1, further comprising:
    a hydrogel reservoir, for providing a hydrogel to the fluid delivery system.

6. The processing system of any of claim 1, further comprising:
    a stabilization liquid reservoir, for providing a stabilizing liquid to the fluid delivery system.

7. The processing system of claim 1, further comprising:
    a flush liquid reservoir, for providing a flush liquid to the fluid delivery system.

8. The processing system of claim 1, further comprising:
    at least one source of electromagnetic radiation, configured for irradiating a substrate positioned on the substrate holder, or the tissue, or both.

9. The processing system of claim 8, wherein the at least one source of electromagnetic radiation is an infrared radiation source.

10. The processing system of claim 8, wherein the at least one source of electromagnetic radiation is an ultraviolet radiation source.

11. The processing system of claim 8, wherein the at least one source of electromagnetic radiation is a visible light radiation source.

12. The processing system of claim 8, wherein the at least one source of electromagnetic radiation is a microwave radiation source.

13. The processing system of claim 1, further comprising:
    a temperature control system for spatially and temporally varying the temperature of a substrate positioned on the substrate holder, or the tissue, or both.

14. The processing system of claim 13, wherein the control system controls the temperature control system.

15. The processing system of claim 1, wherein the fluid delivery system comprises at least one microfluidic device.

16. The processing system of claim 1, wherein the manipulator is configured to vary the distance between the electric field applicator and a substrate positioned on the substrate holder.

17. The processing system of claim 1, wherein the manipulator is configured to vary the azimuthal orientation of the electric field applicator with respect to a substrate positioned on the substrate holder.

18. The processing system of claim 1, wherein the at least one electric field applicator comprises a plurality of microelectrodes, the plurality of microelectrodes being electrically insulated from the processing region.

19. The processing system of claim 1, wherein the electric field is spatially-varying, time-varying, or both.

20. A method of building a tissue from cells, comprising:
supplying a processing medium via a processing chamber having a first end with a substrate positioned in the first end and upon which tissue is to be built, wherein the processing medium is supplied through a fluid delivery system to a processing region of the processing chamber;
supplying cells and fluids through the fluid delivery system to the processing region to be used in building the tissue;
applying a first electrical bias to at least one electric field applicator disposed proximate to the substrate by a distributing bias unit to generate a first electric field, the first electric field being configured to controllably select, transport, orient, arrange, or manipulate cells in the processing region to build the tissue on the substrate;
positioning the at least one electric field applicator with respect to the substrate by a manipulator;
providing electric power to the distributing bias with at least one power supply; and
controlling the at least one electric field applicator, manipulator, and the at least one power supply with a control system.

21. The method of claim 20, further comprising:
applying a second electrical bias by the distributing bias unit to the at least one electric field applicator to generate a second electric field concurrent with the first electric field, the second electric field being different than the first electric field, and configured to controllably select, transport, orient, arrange, or manipulate cells in the processing region to build the tissue on the substrate from the first and second electric fields.

22. The method of claim 20, further comprising:
positioning the at least one electric field applicator, using the manipulator, at a pre-set distance from the substrate.

23. The method of claim 20, further comprising:
positioning the at least one electric field applicator, using the manipulator, at a pre-set azimuthal orientation with respect to the substrate.

24. The method of claim 20, further comprising:
irradiating the tissue with at least one of infrared radiation, visible light radiation, ultraviolet radiation, and microwave radiation.

25. A method for building a tissue from cells, comprising:
positioning a substrate on a first end of a processing chamber and in a processing region of the processing chamber to build tissue upon the substrate from the cells;
supplying a processing medium through a fluid delivery system to the processing region to transport the cells and fluid via the processing medium into the processing region to build tissue upon the substrate;
applying a plurality of electrical biases concurrently to a plurality of electrodes positioned in the processing region to generate a plurality of electric fields in the processing region with each electric field generated by a corresponding electrode; and
adjusting at least one electrical bias to differ from the plurality of electrical biases to generate at least one electric field that differs from the plurality of electric fields to select, transport, orient, arrange, or manipulate cells in the processing region to build the tissue on the substrate.

* * * * *

UNITED STATES PATENT AND TRADEMARK OFFICE
CERTIFICATE OF CORRECTION

PATENT NO. : 9,228,261 B2
APPLICATION NO. : 13/823701
DATED : January 5, 2016
INVENTOR(S) : Jozef Brcka Page 1 of 1

It is certified that error appears in the above-identified patent and that said Letters Patent is hereby corrected as shown below:

In the Specification:
In Col. 2, lines 64-65, "Where the size of the substrate," should read --Where the size of the substrate is equal,--.
In Col. 3, line 57, "An electric field applicator disposed" should read --An electric field applicator is disposed--.
In Col. 5, line 22, "FIG. 8A-8P" should read --FIGS. 8A-8P--.
In Col. 6, line 14, "more of which be selectively" should read --more of which may be selectively--.
In Col. 8, line 42, "indicate a negate" should read --indicate a negative--.
In Col. 8, line 45, "according a selected" should read --according to a selected--.
In Col. 9, line 25, "in FIG. 81," should read --in FIG. 8I,--.

In the Claims:
In Col. 10, line 34, Claim 6, "system of any of claim 1," should read --system of claim 1,--.

Signed and Sealed this
Twenty-fourth Day of May, 2016

Michelle K. Lee
*Director of the United States Patent and Trademark Office*